United States Patent [19]

Winston

[11] Patent Number: 5,415,877
[45] Date of Patent: May 16, 1995

[54] BICARBONATE FUNGICIDE PRODUCT WITH A COMBINATION OF SURFACTANT INGREDIENTS

[75] Inventor: Anthony E. Winston, East Brunswick, N.J.

[73] Assignee: Church & Dwight Co., Inc., Princeton, N.J.

[21] Appl. No.: 171,671

[22] Filed: Dec. 22, 1993

Related U.S. Application Data

[63] Continuation-in-part of Ser. No. 52,266, Apr. 23, 1993.

[51] Int. Cl.$^6$ ............... A01N 59/00; A01N 59/06; A01N 37/02; A01N 41/02
[52] U.S. Cl. ................. 424/717; 424/683; 424/683; 424/686; 424/687; 424/715; 424/716; 514/517; 514/547; 514/709; 514/710; 514/711; 514/769; 514/770; 514/772; 514/772.3; 514/777; 514/778; 514/780; 514/781; 514/782; 504/101
[58] Field of Search ............... 424/716, 716, 717, 405, 424/682, 683, 686, 687; 514/517, 547, 709, 710, 711, 769, 770, 772, 772.3, 777, 778, 780, 781, 782; 504/101

[56] References Cited

U.S. PATENT DOCUMENTS

| 3,576,760 | 4/1971 | Gould et al. | 424/497 |
|---|---|---|---|
| 4,323,680 | 4/1982 | Nakagami et al. | 544/293 |
| 4,599,233 | 7/1986 | Misato et al. | 424/717 |
| 4,661,486 | 4/1987 | Takeshiba et al. | 514/252 |
| 4,952,402 | 8/1990 | Sparks et al. | 424/408 |

FOREIGN PATENT DOCUMENTS

| 53-96319 | 8/1978 | Japan. |
| 60-153785 | 8/1985 | Japan. |

OTHER PUBLICATIONS

Van Nostrand Reinhold Encyclopedia of Chemistry, 4th ed., Van Nostrand Reinhold Company, N.Y., 1984, p. 85.

Primary Examiner—Glennon H. Hollrah
Assistant Examiner—John D. Pak
Attorney, Agent, or Firm—Charles B. Barris

[57] ABSTRACT

The present invention provides a fungicide composition which contains ingredients which are biocompatible for purposes of agricultural applications, and which are harmless to animals and humans. An invention fungicide composition in the form of a dry blend formulation remains non-caking and free-flowing under storage conditions. Illustrative of an invention fungicide composition is a formulation which has a content of sodium bicarbonate, potassium bicarbonate, xanthan gum, dialkylsulfosuccinate salt and alkyl sulfate salt surfactants, and magnesium silicate anti-caking ingredient. The xanthan gum and surfactants function as an effective spreader-sticker and film-forming medium when the composition is diluted with water for agricultural applications.

25 Claims, No Drawings

BICARBONATE FUNGICIDE PRODUCT WITH A COMBINATION OF SURFACTANT INGREDIENTS

CROSS-REFERENCE TO RELATED PATENT APPLICATION

This patent application is a continuation-in-part of patent application Ser. No. 08/052,266, filed Apr. 23, 1993; incorporated herein by reference.

BACKGROUND OF THE INVENTION

The control of phytopathogenic fungi is of great economic importance since fungal growth on plants or on parts of plants inhibits production of foliage, fruit or seed, and adversely affects the overall quality of a cultivated crop.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain an inorganic bicarbonate or carbonate compound. It is known that bicarbonate and carbonate compounds exhibit fungicidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillium italicum* and *Penicillium digitalum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

There remains a continuing need for the development of new and more effective fungicides which possess preventive, curative and systemic activity for the protection of cultivated plants, with a minimum of phytotoxic side effects.

Accordingly, it is an object of this invention to provide a dry blend biocide composition which contains a bicarbonate ingredient exhibiting fungicidal properties, and a combination of surfactant ingredients, and which is harmless to animals and humans.

It is another object of this invention to provide a dry blend fungicide composition which is a non-caking and free-flowing formulation, and which contains particulate ingredients comprising a bicarbonate salt, and a combination of hydrophilic polymer and multiple surfactants which function as a spreader-sticker and film-forming medium when the composition is diluted with water and applied to plant foliage.

Other objects and advantages of the present invention shall become apparent from the accompanying description and examples.

DESCRIPTION OF THE INVENTION

One or more objects of the present invention are accomplished by the provision of a bicarbonate fungicide powder composition which is a dry blend formulation comprising (1) between about 55–98 weight percent of an ingredient selected from alkali metal and ammonium bicarbonates; (2) between about 2–40 weight percent of a combination of surfactant ingredients selected from (a) alkali metal $C_8$–$C_{14}$ dialkyl sulfosuccinate salts, and (b) $C_{10}$–$C_{20}$ alkyl sulfate salts, wherein the weight ratio of sulfosuccinate salt to sulfate salt is between about 2:1 and 1:5; (3) between about 0–20 weight percent of hydrophilic polymer; and (4) between about 0–15 weight percent of anti-caking ingredient.

An invention dry blend fungicide composition can contain about 0.2–20 weight percent of hydrophilic polymer, and about 0.1–15 weight percent of anti-caking ingredient, based on the composition weight.

A dry blend fungicide composition can be diluted with water to form aqueous fungicidal solutions with controlled rheological properties. An aqueous fungicidal solution typically contains between about 0.05–5 weight percent of fungicidal bicarbonate ingredient, based on the solution weight. For most applications the content of bicarbonate ingredient is maintained at a concentration below about one weight percent, as a means of minimizing phytotoxic effects on treated plants which are sensitive to alkaline pH conditions.

An invention dry blend fungicide composition in finely divided form also can be utilized as a dusting powder, which optionally can include a solid diluent such as bentonite, gypsum, diatomaceous earth, and the like. Plant foliage can be treated with a dusting powder, and ambient weather cycles and atmospheric conditions provide sufficient moisture to convert the applied dusting powder to an adherent coating on the plant foliage. A dusting powder preferably has an average particle size diameter between about 1–100 microns, and has a content of submicron particles.

The bicarbonate salt ingredient of an invention fungicide composition is selected from compounds which include sodium bicarbonate, potassium bicarbonate and ammonium bicarbonate. In a further embodiment, the inorganic salt ingredient can include an additional compound selected from sodium carbonate, potassium carbonate, lithium carbonate and ammonium carbonate, in a quantity of about 1–30 weight percent based on the weight of bicarbonate ingredient.

Illustrative of inorganic salt ingredients in a formulation are sodium, potassium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt ingredient normally is determined by pH control considerations when dry blend formulations are being water-diluted. The content of a carbonate salt compound can be varied to control the pH at a desired level in the range of 7.5–12. Water-diluted fungicidal formulations of the present invention tend to have a higher fungicidal activity at higher pH values.

The surfactant ingredients of an invention fungicide composition are selected from (a) alkali metal $C_8$–$C_{14}$ dialkylsulfosuccinate salts such as sodium or potassium dioctyl sulfosuccinate, sodium or potassium dinonyl sulfosuccinate, sodium or potassium didecyl sulfosuccinate, sodium or potassium ditridecyl sulfosuccinate, and the like; and (b) $C_{10}$–$C_{20}$ alkyl sulfate salts such as sodium or potassium decyl sulfate, sodium or potassium dodecyl sulfate, sodium or potassium lauryl sulfate, and the like. The sulfate salts can be in the form of alkyl ether sulfates containing about 1–10 oxyethylene groups in the molecule.

An essential aspect of the invention fungicide compositions is a content of sulfosuccinate and sulfate salt surfactants in a weight ratio of sulfosuccinate salt to sulfate salt between about 2:1 and 1:5, and typically between about 1:1 and 1:3. As demonstrated in Example I, a fungicide composition has a lower fungicidal activity if a combination of sulfosuccinate and sulfate salts is not utilized, or if the combination of surfactants does not have a weight ratio between about 2:1 and 1:5 of sulfosuccinate salt to sulfate salt surfactants.

The anti-caking ingredient of an invention fungicide composition is selected from particulate inorganic and organic compounds which are chemically unreactive with the other ingredients when the composition is in the form of a dry blend formulation. A selected compound preferably has a particulate size distribution less than about 100 microns in diameter.

Suitable anti-caking ingredients include silicious compounds, magnesium compounds, $C_{10}$–$C_{22}$ fatty acid polyvalent metal salt compounds, and the like.

Illustrative of anti-caking ingredients are attapulgite clay, kieselguhr, silica aerogel, silica xerogel, perlite, talc, vermiculite, sodium aluminosilicate, ammonium carbonate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the like.

Preferred anti-caking ingredients include magnesium silicate, magnesium oxide, and the magnesium and aluminum salts of $C_{10}$–$C_{22}$ fatty acids such as palmitic acid, stearic acid and oleic acid.

The use of magnesium silicate as an anti-caking ingredient has particular advantage for purposes of the present invention. Magnesium silicate contributes excellent anti-caking and free-flowing properties to an invention dry blend formulation. Also, when a dry blend formulation is water-diluted, the alkaline pH and the presence of alkali metal compounds cause the conversion of some magnesium silicate to alkali metal silicate. The resultant alkali metal silicate exhibits strong adhesive activity when the aqueous formulation is applied to plant foliage.

The anti-caking ingredient normally is utilized in the least quantity which will effect the desired degree of anti-caking and free-flowing properties. Typically the anti-caking ingredient is incorporated in a dry blend formulation in a quantity between about 0.1–3 weight percent, based on the composition weight.

A preferred dry blend fungicide composition of the present invention is one containing sodium or potassium bicarbonate, xanthan gum, sodium sulfosuccinate dialkyl ester, sodium alkyl sulfate salt, and magnesium silicate ingredients.

Another significant advantage of the selected ingredients in a present invention fungicide composition is the solid form of each ingredient at ambient temperatures. This permits the formulation of a fungicide composition which is a free-flowing dry powder. All of the ingredients are readily dispersible in water to form an aqueous solution suitable for spray applications.

The ingredients in an invention fungicide composition can be selected to include nitrogen, phosphorus and potassium elements in a ratio that qualifies the composition to function as a fertilizer in addition to its function as a fungicide, when applied to cultivated crops. When a water-diluted fungicide composition containing fertilizer elements is sprayed on plant foliage, there is direct absorption of the fertilizer elements into the leaves.

In another embodiment this invention provides a fungicidal fertilizer powder composition which is a dry blend formulation comprising (1) between about 55–98 weight percent of an ingredient selected from alkali metal and ammonium bicarbonates; (2) between about 2–40 weight percent of a combination of surfactant ingredients selected from (a) alkali metal $C_8$–$C_{14}$ dialkyl sulfosuccinate salts, and (b) $C_{10}$–$C_{20}$ alkyl sulfate salts, wherein the weight ratio of sulfosuccinate salt to sulfate salt is between about 2:1 and 1:5; (3) between about 0–20 weight percent of hydrophilic polymer; (4) between about 0–15 weight percent of anti-caking ingredient; and (5) between about 5–30 weight percent of an ingredient selected from phosphorus-containing compounds; wherein the composition ingredients have a formulated ratio of nitrogen, phosphorus and potassium elements.

The formulated ratio depends on the intended application. A typical ratio is 10-15-10. Besides nitrogen, phosphorus and potassium, an invention fungicidal fertilizer composition can contain trace elements, and other essential elements as exemplified by sulfur as contained in a compound such as sodium bisulfite or thiourea.

A present invention fungicide composition can be prepared by dry-blending the particulate ingredients using conventional equipment. In one method, the bicarbonate, hydrophilic polymer and surfactant are pre-blended, and subsequently the anti-caking ingredient is added to the pre-blend in a rotating type mixer before any agglomeration of particles occurs.

In another method, the anti-caking ingredient is pre-blended with the hydrophilic polymer, and the pre-blend then is admixed with the other particulate ingredients.

Without the incorporation of an anti-caking ingredient, the particulate ingredients of a dry blend fungicide composition tend to agglomerate on standing, and the free-flow character of the composition is diminished.

An invention fungicide composition can include one or more other biologically active ingredients, such as those which exhibit herbicidal, insecticidal or plant growth regulating activity.

A fungicide composition of the present invention has a novel combination of properties for the practice of pesticide control in agricultural and horticultural applications.

The bicarbonate ingredient exhibits fungicidal properties, and the efficacy of any additional included organic pesticide ingredient usually is enhanced by the presence of the bicarbonate ingredient. A lesser quantity of optional pesticide ingredient can be employed to achieve a desired degree of pest control.

A present invention fungicide composition can be formulated to exhibit no phytotoxicity, or to minimize the toxic effects of salt stress on plants by the bicarbonate ingredient.

A present invention fungicide composition provides particular advantage for the control of infectious phytopathogenic fungi which thrive under acidic soil conditions.

All of the fungicide composition ingredients are biocompatible when the composition is applied in an agricultural environment. The bicarbonate, hydrophilic polymer, surfactant and anti-caking ingredients are all harmless to animals and humans.

A significant feature of a present invention dry blend fungicide composition is the presence of a combination of specific surfactant ingredients, which function as a spreader-sticker medium when the fungicide composition is applied to plant foliage as a water-diluted solution. An applied aqueous solution forms an adherent coating of ingredients on plant foliage or fruit. The surfactant ingredients aid in spreading and sticking the fungicide composition ingredients to the foliage or fruit to which it is applied. The hydrophilic polymer ingredient increases the amount of aqueous fungicide composition which adheres to the plant surfaces because of its static high apparent viscosity. During a spraying procedure, the hydrophilic polymer ingredient contributes a low pseudoplastic viscosity to the spray solution, which facilitates the spraying action. After spraying, the applied coating resists drifting under wind conditions, and exhibits humectant properties in addition to enhanced fungicidal activity.

Another important advantage of a preferred invention fungicide composition derives from the water-solubility of the main ingredients. A coating of an invention fungicide composition on plant foliage or fruit can be removed readily by water-washing. Conventional fungicide compositions which contain a petroleum-based spreader-sticker ingredient leave an oily residue on treated plant foliage or fruit which is difficult to remove.

The following examples are further illustrative of the present invention. The components and specific ingredients are presented as being typical, and various modifications can be derived in view of the foregoing disclosure within the scope of the invention.

EXAMPLE I

This Example illustrates an enhanced fungicidal effect exhibited by fungicide products in accordance with the present invention.

A. Leaflets, heavily infected with powdery mildew, are detached from greenhouse-grown Mary Devor cultivar roses. The stem end of the leaflet is placed in an open aluminum pan containing 2% water agar. The leaflets are then sprayed to run-off with a solution of a test formulation. After 18–24 hours the quantity of powdery mildew remaining is scored as follows:

0 = no mildew, 1 = 10% coverage, 2 = 30% coverage, 3 = 50% coverage, 4 = 70% coverage, 5 = 90 + % coverage.

Each test formulation is evaluated twice using 10 replicates. The following formulations are evaluated.

|  | Control A | Control B | Invention Composition 1 | Invention Composition 2 | Control C |
|---|---|---|---|---|---|
| NaDOSS[1] | 5.00% | 3.75% | 2.5% | 1.25% | 0.00% |
| SLS[2] | 0.00 | 1.25 | 2.5 | 3.75 | 5.00 |
| KHCO$_3$ | 20.00 | 20.00 | 20.00 | 20.00 | 20.00 |
| Water | 75.00 | 75.00 | 75.00 | 75.00 | 75.00 |

[1]Sodium dioctyl sulfosuccinate
[2]Sodium lauryl sulfate

The prepared solutions are diluted with water to a 0.5 weight percent content of potassium bicarbonate before application to the rose leaflets.

The results of the comparative tests are as follows:

|  | MEAN SCORE | STD. DEV. | SIG. |
|---|---|---|---|
| Water Control | 5.0 | 0 | a[1] |
| Control A | 2.5 | 1.11 | b |
| Control B | 2.5 | 1.15 | b |
| Inv. Comp. 1 | 1.75 | 0.91 | c |
| Inv. Comp. 2 | 1.65 | 0.81 | c |
| Control C | 2.95 | 1.28 | b |

[1]Products with different letters are significantly different (p, 0.05) based on Duncan's multiple range test.

The results demonstrate that the products containing combinations of sodium dioctyl sulfosuccinate and sodium lauryl sulfate in the ratio of between about 2:1 and 1:5 provide synergistic activity in their ability to promote the fungicidal activity of bicarbonates.

B. Additional formulations are prepared as follows:

|  | Control D | Control E | Control F | Invention Composition 3 | Invention Composition 4 |
|---|---|---|---|---|---|
| NaDNSS[1] | 5.0% | 0.0% | 0.0% | 2.5% | 0.0% |
| NaDTSS[2] | 0.0 | 5.0 | 0.0 | 0.0 | 2.5 |
| SLS[3] | 0.0 | 0.0 | 5.0 | 2.5 | 2.5 |
| KHCO$_3$ | 20.0 | 20.0 | 20.0 | 20.0 | 20.0 |
| Water | 75.0 | 75.0 | 75.0 | 75.0 | 75.0 |

[1]Sodium dinonyl sulfosuccinate
[2]Sodium ditridecyl sulfosuccinate
[3]Sodium lauryl sulfate The solutions are diluted with water to a 0.5 weight percent content of potassium bicarbonate before application to the leaflets.

The results of the comparative tests are as follows:

|  | MEAN SCORE | STD. DEV. | SIG. |
|---|---|---|---|
| Water Control | 4.95 | 0.22 | a |
| Control D | 4.70 | 0.57 | ab |
| Control E | 4.75 | 0.64 | ab |
| Control F | 3.75 | 1.07 | c |
| Inv. Comp. 3 | 1.80 | 1.11 | d |
| Inv. Comp. 4 | 2.05 | 0.94 | d |

The data demonstrate that the invention formulations exhibit an enhanced fungicidal activity when a combination of sulfosuccinate and sulfate surfactants are utilized.

Additional formulations are prepared as follows:

|  | Control G | Control H | Invention Composition 5 |
|---|---|---|---|
| NaDOSS[1] | 5.0% | 0.0% | 2.5% |
| SDS[2] | 0.0 | 5.0 | 2.5 |
| KHCO$_3$ | 20.0 | 20.0 | 20.0 |
| Water | 75.0 | 75.0 | 75.0 |

[1]Sodium dioctyl sulfosuccinate
[2]Sodium oleyl sulfate

The solutions are diluted with water to a 0.5 weight percent content of potassium bicarbonate before application to the leaflets.

The results of the comparative tests are as follows:

|  | MEAN SCORE | STD. DEV. | SIG. |
|---|---|---|---|
| Water Control | 4.70 | 0.57 | a |
| Control G | 4.55 | 0.89 | a |
| Control H | 1.65 | 1.14 | b |
| Inv. Comp. 5 | 0.90 | 0.79 | c |

The results demonstrate that the Invention 5 product containing a combination of sodium dioctyl sulfosuccinate and sodium oleyl sulfate in the ratio of 1:1 provides synergistic activity in promoting the fungicidal activity of potassium bicarbonate.

EXAMPLE II

This Example illustrates the preparation of a dry blend fungicidal formulation in accordance with the present invention.

|  | Parts |
|---|---|
| potassium bicarbonate | 85.4 |
| potassium carboxymethyl-cellulose[1] | 10.0 |
| potassium didecyl sulfosuccinate | 1.0 |
| potassium lauryl sulfate | 3.0 |
| magnesium stearate | 0.6 |

[1] Aldrich Chemical Co., CMC of 3000–6000 centipoises, intrinsic viscosity of 2% aqueous solution at 25° C.

The magnesium stearate is admixed with a pre-blend of the other ingredients to form a non-caking free-flowing powder. The magnesium stearate has an average particle size of about 10 microns.

The powder is suspended in water to form an aqueous emulsion with a 0.3 weight percent content of potassium bicarbonate. The diluted formulation is tested as a fungicide medium against plant foliage infected with powdery mildew. The fungicidal medium is 100% effective in mildew eradication, and prevents re-infection.

EXAMPLE III

This Example illustrates the preparation of a fungicide powder composition in accordance with the present invention.

A free-flowing blend of the following ingredients is prepared in a cone mixer:

|  | Parts |
|---|---|
| sodium bicarbonate | 50.0 |
| potassium bicarbonate | 35.0 |
| xanthan gum | 10.0 |
| sodium dioctyl sulfosuccinate | 2.0 |
| sodium lauryl sulfate | 3.0 |
| magnesium silicate | 0.5 |

The formulated powder is diluted with water by dispersing 2 parts of the powder blend into 100 parts of water. The resulting solution is sprayed onto plant foliage where it forms an adherent coating on the foliage surfaces.

The formulated powder remains free-flowing when it is stored in a closed container at ambient temperature for six months. The same formulation without an anti-caking ingredient undergoes some agglomeration of particles and loss of free-flow capability under the same storage conditions.

EXAMPLE IV

This Example illustrates the preparation of a dry blend fungicidal formulation which contains a mixture of bicarbonate compounds.

|  | Parts |
|---|---|
| potassium bicarbonate | 25 |
| sodium bicarbonate | 25 |
| ammonium bicarbonate | 25 |
| carrageenan | 12 |
| potassium dinonyl sulfosuccinate | 2 |
| potassium dodecyl sulfate | 2 |
| sodium phthalate | 4 |

The particulate ingredients are dry blended to form a non-caking free-flowing powder.

The ingredients are added to the water to form an aqueous solution which has a 0.5 weight percent content of bicarbonate ingredients.

The formulation is more effective than a comparative formulation containing a single bicarbonate Compound, for controlling a broad range of foliar and soil-born resistant fungi.

EXAMPLE V

This Example illustrates the preparation of a fungicidal fertilizer composition for application to plant foliage and soil.

|  | Parts |
|---|---|
| potassium bicarbonate | 55.0 |
| ammonium bicarbonate | 20.0 |
| xanthan gum | 5.0 |
| sodium ditridecyl sulfosuccinate | 2.0 |
| sodium lauryl sulfate | 3.0 |
| ammonium nitrate | 15.00 |
| dipotassium orthophosphate | 5.0 |
| copper oxide | 2.0 |

The copper oxide (0.1–10 micron range) is pre-blended with the particulate ammonium nitrate ingredient, and the pre-blend then is combined with the other ingredients in a rotary mixer to form a non-caking free-flowing powder.

The powder is dispersed in water to form a solution which has a 0.5 weight percent content of potassium bicarbonate.

A container of the solution is connected to agricultural sprayer equipment, and sprayed through a hollow cone spray nozzle at a pressure of 250 psi. The spray droplet size is 100–150 microns. A field of ornamental evergreen saplings is sprayed with the solution, and is effective for preventing fungal infection of the trees, and for promoting vigorous growth.

EXAMPLE VI

This Example illustrates the preparation of a dry blend fungicidal formulation which contains a high content of surfactant ingredients in accordance with the present invention.

| | Parts |
|---|---|
| potassium bicarbonate | 30.0 |
| sodium bicarbonate | 29.5 |
| sodium lauryl sulfate | 25.0 |

| | Parts |
|---|---|
| sodium dioctyl sulfosuccinate | 15.0 |
| magnesium oxide | 0.5 |

The particulate ingredients are dry blended to form a non-caking free-flowing powder.

The powder formulation is diluted with water to form an aqueous solution which has a 0.2 weight percent of bicarbonate ingredients.

The aqueous formulation is particularly effective for controlling powdery mildew on ornamentals and field crops.

What is claimed is:

1. A bicarbonate fungicide powder composition which is a dry blend formulation comprising (1) between about 55–98 weight percent of an ingredient selected from alkali metal and ammonium bicarbonates; (2) between about 2–40 weight percent of a combination of surfactant ingredients selected from (a) alkali metal $C_8$–$C_{14}$ dialkyl sulfosuccinate salts, and (b) $C_{10}$–$C_{20}$ alkyl sulfate salts, wherein the weight ratio of sulfosuccinate salt to sulfate salt is between about 2:1 and 1:5; (3) between about 0–20 weight percent of hydrophilic polymer; and (4) between about 0–15 weight percent of anti-caking ingredient.

2. A composition in accordance with claim 1 which has about a 55–98 weight percent content of sodium bicarbonate, based on the composition weight.

3. A composition in accordance with claim 1 which has about a 55–98 weight percent content of potassium bicarbonate, based on the composition weight.

4. A composition in accordance with claim 1 which has about a 55–98 weight percent content of ammonium bicarbonate, based on composition weight.

5. A composition in accordance with claim 1 which has a 55–98 weight percent content of sodium bicarbonate and potassium bicarbonate, based on the composition weight.

6. A composition in accordance with claim 1 which has 55–98 weight percent content of sodium bicarbonate and ammonium bicarbonate, based on the composition weight.

7. A composition in accordance with claim 1 which has a 55–98 weight percent content of sodium bicarbonate, potassium bicarbonate and ammonium bicarbonate, based on the composition weight.

8. A composition in accordance with claim 1 which additionally contains between about 1–30 weight percent of an ingredient selected from alkali metal and ammonium carbonates, based on the weight of bicarbonate ingredient.

9. A composition in accordance with claim 1 wherein one surfactant ingredient is sodium dioctyl sulfosuccinate.

10. A composition in accordance with claim 1 wherein one surfactant ingredient is sodium lauryl sulfate.

11. A composition in accordance with claim 1 which has about a 0.5–20 weight percent content of hydrophilic polymer ingredient, based on the composition weight.

12. A composition in accordance with claim 1 wherein the hydrophilic polymer ingredient comprises a hydrocolloid gum.

13. A composition in accordance with claim 1 wherein the hydrophilic polymer ingredient comprises a cellulosic derivative.

14. A composition in accordance with claim 1 wherein the hydrophilic polymer ingredient comprises a starch derivative.

15. A composition in accordance with claim 1 wherein the hydrophilic polymer ingredient comprises a polyacrylamide derivative.

16. A composition in accordance with claim 1 wherein the hydrophilic polymer ingredient comprises a maleic anhydride copolymer derivative.

17. A composition in accordance with claim 1 wherein the hydrophilic polymer ingredient comprises xanthan gum or guar gum.

18. A composition in accordance with claim 1 which has about a 0.1–15 weight percent content of anti-caking ingredient, based on the composition weight.

19. A composition in accordance with claim 1 wherein the anti-caking ingredient is selected from silicious compounds, magnesium compounds, and $C_{10}$–$C_{22}$ fatty acid polyvalent metal salt compounds.

20. A composition in accordance with claim 1 wherein the anti-caking ingredient is magnesium silicate.

21. A composition in accordance with claim 1 wherein the anti-caking ingredient is magnesium oxide.

22. A composition in accordance with claim 1 wherein the anti-caking ingredient is copper oxide.

23. A composition in accordance with claim 1 wherein the anti-caking ingredient is magnesium stearate.

24. A composition in accordance with claim 1 wherein the anti-caking ingredient is colloidal silica.

25. An aqueous fungicide formulation which comprises a claim 1 composition which is diluted with water to a bicarbonate content between about 0.05–5 weight percent, based on the formulation weight.

* * * * *

UNITED STATES PATENT AND TRADEMARK OFFICE
CERTIFICATE OF CORRECTION

PATENT NO.  : 5,415,877
DATED       : May 16, 1995
INVENTOR(S) : Winston et al

It is certified that error appears in the above-indentified patent and that said Letters Patent is hereby corrected as shown below:

On the title page, item [75]: Inventors should read;

-- Anthony E. Winston, East Brunswick; Keith A. Jones, Lambertville; and Alfredo Vinci, Dayton; all of New Jersey --

Signed and Sealed this

Twelfth Day of August, 1997

Attest:

BRUCE LEHMAN

Attesting Officer

Commissioner of Patents and Trademarks